(12) United States Patent
Jiang et al.

(10) Patent No.: US 9,011,917 B2
(45) Date of Patent: Apr. 21, 2015

(54) METHOD FOR ENZYMATIC TREATMENT, DEVICE AND KIT USED THE SAME

(71) Applicant: Industrial Technology Research Institute, Hsinchu (TW)

(72) Inventors: Ching-Chuan Jiang, Taipei (TW); Chun-Jen Liao, Taipei (TW); Wen-Hsiang Chang, Hsinchu (TW); Huang-Chi Chen, Chiayi County (TW); Wei-Ju Liao, Taichung (TW); Wen-Hsi Wang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 14/162,610

(22) Filed: Jan. 23, 2014

(65) Prior Publication Data

US 2014/0142521 A1    May 22, 2014

Related U.S. Application Data

(62) Division of application No. 13/614,766, filed on Sep. 13, 2012.

(60) Provisional application No. 61/608,378, filed on Mar. 8, 2012.

(30) Foreign Application Priority Data

May 4, 2012   (TW) ............................. 101115922 A (51) Int. Cl.
*A61M 37/00*   (2006.01)
*C12N 5/07*    (2010.01)
(Continued)

(52) U.S. Cl.
CPC ................ *A61M 37/00* (2013.01); *C12N 5/06* (2013.01); *C12M 1/40* (2013.01); *C12M 21/08* (2013.01); *C12M 23/20* (2013.01); *C12M 35/08* (2013.01)

(58) Field of Classification Search
IPC ............ A61M 37/00; C12M 1/40,35/08, 21/08, C12M 23/20; C12N 5/06
See application file for complete search history.

(56) References Cited

U.S. PATENT DOCUMENTS

| 5,462,739 | A | 10/1995 | Dan et al. |
| 5,941,859 | A | 8/1999 | Lerman |

(Continued)

FOREIGN PATENT DOCUMENTS

| CN | 1520306 A | 8/2004 |
| EP | 2065016 A1 | 6/2009 |

OTHER PUBLICATIONS

Barbir et al., "Effects of enzymatic digestion on compressive properties of rat intervertebral discs", Journal of Biomechanics, 43 (2010), pp. 1067-1073.

(Continued)

*Primary Examiner* — Rosanne Kosson
(74) *Attorney, Agent, or Firm* — Birch, Stewart, Kolasch & Birch, LLP (57) ABSTRACT

One embodiment provides a method for enzymatic treatment, including the steps of forming a closed space on a local tissue area with a device and infusing an enzyme solution into the closed space for enzymatic treatment. The method according to the embodiment is capable of treating the local tissue area with enzymes for enhancing cell proliferation in the treated tissue area and preventing damage of the adjacent normal tissues. A device and kit used for the method are also provided.

13 Claims, 6 Drawing Sheets

(51) Int. Cl.
*C12M 1/40* (2006.01)
*C12M 3/00* (2006.01)
*C12M 1/00* (2006.01)
*C12M 1/42* (2006.01)

(56) References Cited

U.S. PATENT DOCUMENTS

| | | | |
|---|---|---|---|
| 6,436,078 B1 * | 8/2002 | Svedman | 604/313 |
| 7,184,827 B1 | 2/2007 | Edwards | |
| 7,559,923 B2 | 7/2009 | Seward et al. | |
| 7,731,685 B2 | 6/2010 | Ragheb et al. | |
| 7,963,956 B2 | 6/2011 | Kunst | |

OTHER PUBLICATIONS

Diao et al., "Improved Cartilage Regeneration Utilizing Mesenchymal Stem Cells in TGF-beta1 Gene-Activated Scaffolds", Tissue Engineereing: Part A, vol. 15, No. 9, (2009), pp. 2687-2699.

Eliasson et al., "Rat Achilles tendon healing: mechanical loading and gene expression", J Appl Physiol 107, Jun. 18, 2009, pp. 399-407.

Gilbert et al., "Enhanced tissue integration during cartilage repair in vitro can be achieved by inhibiting chondrocyte death at the wound edge", Tissue Engineering: Part A, vol. 15, No. 7, (2009), pp. 1739-1750.

Hardmeier R. et al., "Effects of mechanical loading on collagen propeptides processing in cartilage repair", J. Tissue Eng. & Regen Med 2010; 4: pp. 1-11.

Kim et al., "Evaluation of early osteochondral defect repair in a rabbit model utilizing fourier transform-infrared imaging spectroscopy, magnetic resonance imaging, and quantitative T2 mapping", Tissue Engineering: Part C, vol. 16, No. 3, (2010), pp. 355-364.

Nakase et al., "Facilitated tendon-bone healing by local delivery of recombinant hepatocyte growth factor in rabbits", Arthroscopy: The Journal of Arthroscopic and Related Surgery, vol. 26, No. 1, Jan. 2010, pp. 84-90.

Schulze-Tanzil, G, "Activation and dedifferentiation of chondrocytes: implications in cartilage injury and repair", Annals of Anatomy, 191, (2009), pp. 325-338.

* cited by examiner

METHOD FOR ENZYMATIC TREATMENT, DEVICE AND KIT USED THE SAME

CROSS REFERENCE TO RELATED APPLICATIONS

This application is a Divisional of pending U.S. patent application Ser. No. 13/614,766, filed Sep. 13, 2012, and entitled "Method For Enzymatic Treatment, Device And Kit Used The Same", which claims the priority of TW 101115922, filed May 4, 2012, which claims the priority of U.S. Provisional Application No. 61/608,378, filed Mar. 8, 2012. The disclosure of the applications is incorporated herein by reference.

TECHNICAL FIELD

The technical field relates to a method for enzymatic treatment and a device and kit used the same.

BACKGROUND

Tissue defects usually result from injuries, aging, disorders or similar factors. The soft tissue defect, such as osteoarthritis, is commonly found in tissue defects. It is well-known to treat osteoarthritis with drug administration (like nonsteroidal anti-inflammatory drugs (NSAIDs)) to relieve pain and inflammation or with surgery (like abrasion arthroplasty or debridement and lavage) to maintain the smoothness of the joint cartilage tissue surface and avoid joint degeneration from the abrasion between the cartilages in the joint. A severe destructive joint may be surgically replaced with an artificial joint. However, NSAIDs administration may cause side effects, like gastrospasm, diarrhea, ulcer, bleeding, or the like. Meanwhile, surgery may cause complications and the recovery after surgery should be considered.

A treatment of osteoarthritis by implanting osteochondral cells has been suggested. First, a donor's osteochondral cores are purified with a centrifuge to remove blood, lipids or other antigen-like substances or contaminants. The purified osteochondral cells are then implanted into a joint defect region of the receptor for enhancing the cartilage and bone in the defect region to grow and repair itself. The treatment can also reduce the probability of diseases being transferring to receptors.

However, for the purpose of increasing the efficiency of tissue repair and decreasing side effects from surgery and drug administration, developing novel methods and devices for tissue repair is needed.

SUMMARY

A detailed description is given in the following embodiments with reference to the accompanying drawings.

One embodiment provides a method for enzymatic treatment, comprising forming a closed space on a local tissue area and infusing an enzyme solution into the closed space.

Another embodiment provides a device for enzymatic treatment, in which the device comprises a hollow cavity including a first side and a second side at the opposite side. The first and second sides respectively comprise at least one of openings. The characteristic of the device is to form a closed space on a local tissue area for enzyme solution reserve and enzymatic treatment.

Exemplary embodiment provides a kit for treatment of tissue defects, comprising the said device with an enzyme solution.

BRIEF DESCRIPTION OF THE DRAWINGS

The disclosure can be more fully understood by reading the subsequent detailed and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment, the enzymatic treatment is performed on a local tissue area, which makes the extracellular matrix loose and cells free and therefore enhances cell proliferation in the tissue area. In addition, in accompany with cell proliferation, a large amount of extracellular matrix is produced, which further enhances tissue repair.

The method for enzymatic treatment in one embodiment comprises the steps of forming a closed space on a local tissue area and infusing an enzyme solution into the closed space.

The "close space" recited herein refers to a limited space which does not allow inside fluids to flow out. The closed space according to the embodiment may be formed on a local tissue area with any material or device. In one example, the closed space is formed by immobilizing a device on a local tissue area.

The device in one embodiment may comprise a hollow cavity which includes a first side and a second side. The second side is opposed to the first side and each side comprises at least one of openings.

Figure 1A:
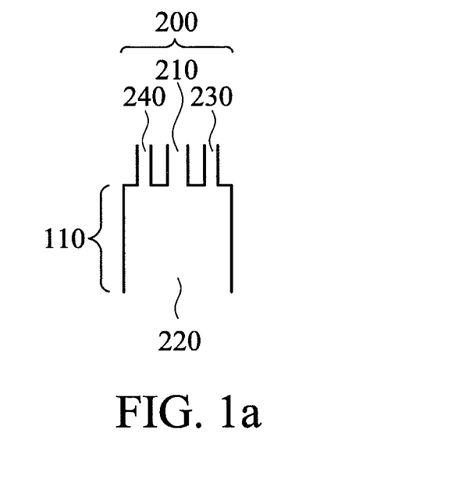
FIG. 1a is a schematic view of hollow cavity in one embodiment.

One example of the device is shown as FIG. 1a. The hollow cavity 110 comprises a first side 200 and a second side 220 at the opposite side. The first side 200 comprises as least one of openings, such as an in-put opening 230, an out-put opening 240 and a fixation opening 210. The second side 220 comprises at least one of openings for immobilization on a local tissue area to form a closed space.

The hollow cavity recited herein may be in any form without a specific limitation. The hollow cavity is in a form of hollow cylinders for convenient operation. The size of the hollow cavity can be suitably designed according to the tissue type or location, but the hollow cavity is a hollow cylinder with an inside diameter of about 5~30 mm.

In the example shown in FIG. 1a, the fixation opening 210 at the first side is for the penetration of pre-fixation equipment. The pre-fixation equipment recited herein refers to an instrument or apparatus fixed in the tissue, which is desired for the enzymatic treatment before the closed space is formed. Because of the pre-fixation, the hollow cavity is capable of accurately being immobilized on the tissue area desired for the enzymatic treatment. The pre-fixation equipment recited herein is not specifically limited, which may be a known instrument for tissue fixation in clinics, such as a Kirschner pin (k-pin).

According to the embodiment, the tissue area for enzymatic treatment may be determined by using clinical tissue detection techniques, such as autoradiography, fluorescent imaging, ultrasound imaging, magnetic resource imaging (MRI), endoscope, or the like, but are not limited thereto.

In the example shown in FIG. 1a, the first side of the hollow cavity comprises an in-put opening 230 for infusing the enzyme solution into the closed space and an out-put opening 240 for extracting and removing the fluid out of the closed space. The in-put and out-put openings may be present at any side of the fixation opening if necessary. The arrangement shown in FIG. 1a is for easy understanding but the embodiment is not limited thereto. For convenient operation, the in-put and out-put openings are flanked to the fixation opening.

In one embodiment, the inside diameter of the in-put and out-put openings can be suitably adjusted according to the size of the hollow cavity, the tissue location, the enzyme properties or similar factors. The inside diameter of the in-put and out-put openings is 1~2 mm but is not limited thereto.

In the example shown in FIG. 1a, the opening 220 at the second side is used for immobilization on the tissue in order to form a closed space between the hollow cavity and the tissue surface. The inside diameter and length of the opening 220 at the second side is not specifically limited, which can be appropriately adjusted according to the size of the hollow cavity, the tissue location, the tissue type or similar factors. The inside diameter of the opening 220 at the second side is identical to that of the hollow cavity and the length of the opening 220 is about 5~20 mm.

Figure 1B:
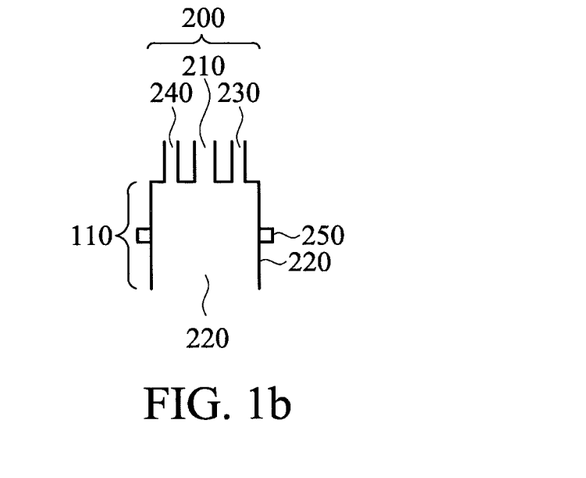
FIG. 1b is a schematic view of hollow cavity in one embodiment.
Figure 2:
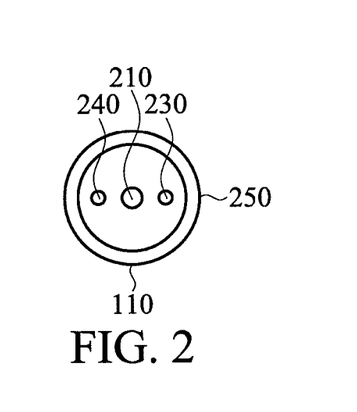
FIG. 2 shows a top view of the hollow cavity in one embodiment.

In another embodiment, the hollow cavity may further comprise a extrusion 250 both flanks of the second side to limit the depth of the opening 220 in the tissue and assist in the immobilization of the hollow cavity on the tissue surface (FIGS. 1b & 2). The location and length of the extrusion at the flank of the second side can be suitably arranged if necessary. For convenient operation, the extrusion may be at the flank of the second side at a distance of about 3~5 mm from the end of the second side 220 and at a length of about 3~5 mm from the flank of the second side 220. extrusions on both flanks of the second side The hollow cavity according to the disclosure, because contacting tissues, is consisted of biocompatible materials. The biocompatible material may comprise polyether ether ketone (PEEK), stainless steel or silicone, but are not limited thereto.

Figure 4:
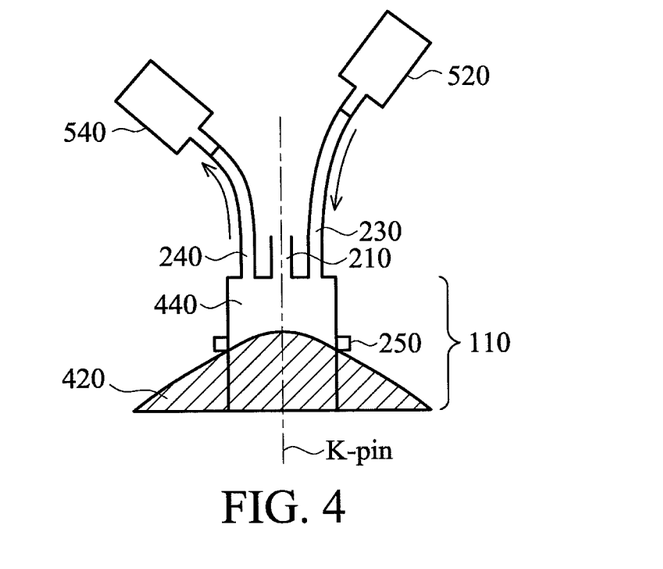
FIG. 4 shows a device immobilized on a tissue surface in one embodiment.

In one embodiment, the device according to the disclosure may further comprise an infusion element 520 comprising a container part for enzyme solution reserve and an infusion opening. For instance, the infusion element may be a syringe. In the example, the infusion opening may be connected to the in-put opening 230 of the hollow cavity 110, allowing the enzyme solution in the container part of the infusion element 520 to flow into the hollow cavity 110 through the infusion opening and the in-put opening 230.

In the embodiment, the device may further comprise an extraction element 540 comprising an extraction part for extracting out fluids in the closed space and an extraction opening. The extraction element may be a syringe for instance. In the example, the extraction opening of the extraction element 540 may be connected with the out-put opening 240 of the hollow cavity 110, allowing the fluid in the closed space to be extracted out through the extraction opening and the out-put opening 240 of the hollow cavity 110.

Figure 3:
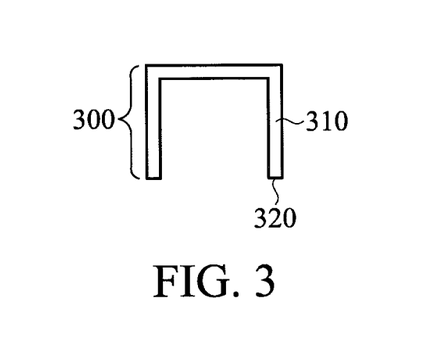
FIG. 3 show examples of an auxiliary element in one embodiment.

In one embodiment, the device according to the disclosure may further comprise an auxiliary element, as shown in FIG. 3, for assisting in the immobilization of the hollow cavity 110 on the tissue area. In this example, the auxiliary element 300 comprises a cap body 310 and an opening 320. In the example, the opening 320 is designed to fully cover the extrusion 250 of the hollow cavity 110, so that the auxiliary element 300 can completely cover the hollow cavity 110.

In one embodiment, when the hollow cavity 110 is put on the tissue surface in a manner of the pre-fixation equipment penetrating through the fixation opening 210, the operator may cover the hollow cavity 110 with the auxiliary element 300 and knock the cap body 310 to make the second side 110 of the hollow cavity 110 into the tissue to immobilize the hollow cavity to the tissue area and form a closed space for the enzymatic treatment.

The shape of the auxiliary element according to the embodiment is not specifically limited but can be appropriately adjusted according to the tissue type, the shape of the hollow cavity, or similar conditions. For convenient operation, the auxiliary element can be a circle cap with a diameter of about 5~10 mm and a height of about 5~30 mm.

The infusion element, extraction element and auxiliary element according to the disclosure can be consisted of any material, while the material does not react with the enzyme solution. In one example of the disclosure, the infusion element, extraction element and auxiliary element are consisted of biocompatible materials, such as polyether ether ketone (PEEK), stainless steel or silicone, but are not limited thereto.

The method according to the embodiment comprises an enzyme solution infusion through the infusion element and fluid extraction through the extraction element. Accordingly, the fluid in the closed space after the enzymatic treatment may comprise the enzyme solution, the interstitial fluid, dead cells or tissues, free cells or the like. Because the enzymatic treatment removes the dead cells and tissues and makes the extracellular matrix loosen and cells free, the cell proliferation at the tissue area can be enhanced and tissue repair can be further promoted. Moreover, because the enzymatic treatment is performed in a closed space, the enzyme solution does not flow out to destroy the adjacent normal tissues. Therefore, according to the embodiment, a substantial local tissue treatment can be achieved with little tissue damages and less operation.

The enzyme solution recited herein refers to a solution containing an enzyme(s) with the ability of digesting tissues and enhancing tissue regeneration. More specific, the enzyme solution may comprise collagenase, hyaluronidase, trypsin, lipase, proteinase or other enzymes or peptides with similar functions or a combination thereof.

The method for enzymatic treatment according to the embodiment may be performed in vitro or in vivo. For increasing comfort and decreasing danger from in vitro sampling procedures, the method according to the embodiment is performed in vivo. Accordingly, the method according to the embodiment can be performed at a body temperature of animals or at room temperature, but it is not limited thereto.

The time and the enzyme concentration for the enzymatic treatment according to the embodiment are not specifically limited, which can be suitably modified according to the tissue type, the extent of the tissue defect, the development of the disease or the like. The time for the enzymatic treatment can last for 5 minutes to 1 hour, or 5 to 30 minutes. The enzyme concentration is 2~5 U/ml, or 2~3 U/ml.

The tissue for the enzymatic treatment of the embodiment may comprise animal cartilage tissues, bone tissues, nerve tissues, or the like, particularly the cartilage tissue of degenerative arthritis, but are not limited thereto. The animal recited herein may comprise mammals, such as mice, rats, cats, dogs, rabbits, pigs, cows, goats, horses, primates, or humans.

One example of the embodiment provides a kit for treatment of tissue defects comprising the device for enzymatic treatment and the enzyme solution as described above. The kit may further comprise an instruction manual providing the procedure of using the device and the enzyme solution.

EXAMPLES

Example 1

Implantation Test of Cartilage and Bone Tissues

Cartilage and bone tissues (3 mm-diameter shin) of a porcine knee joint were categorized into experimental and control groups. The experimental group cartilage and bone tissues were immerged into 2.6 U/ml of liberase (one of collagenases) solution (Roche) at 37° C. for 20 minutes. The treated tissue was washed with saline and implanted into a mouse subcutaneous tissue. The control group cartilage and bone tissues were immerged in saline at 37° C. for 20 minutes. The treated tissues were washed with saline and implanted into another mouse subcutaneous tissue.

Figure 5A:
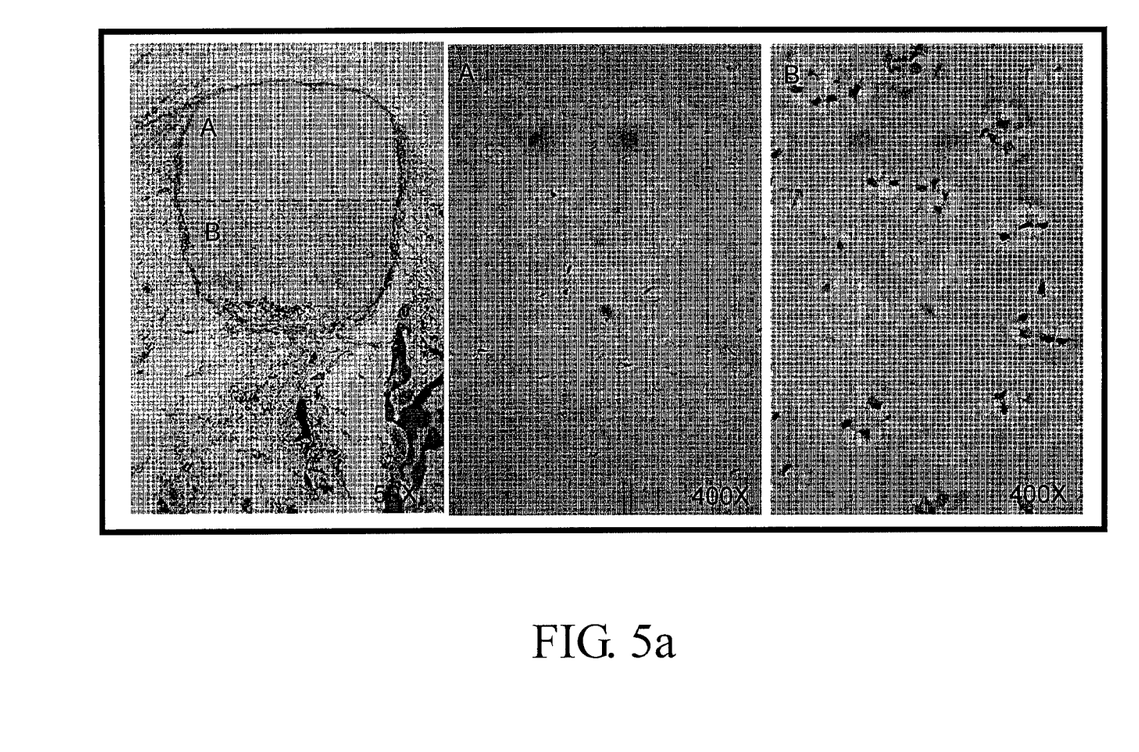
FIG. 5a is a microscopic photograph showing the cell growth of an enzyme-untreated cartilage and bone tissues which had been implanted into mouse subcutaneous tissues for one month in one comparative example.
Figure 5B:
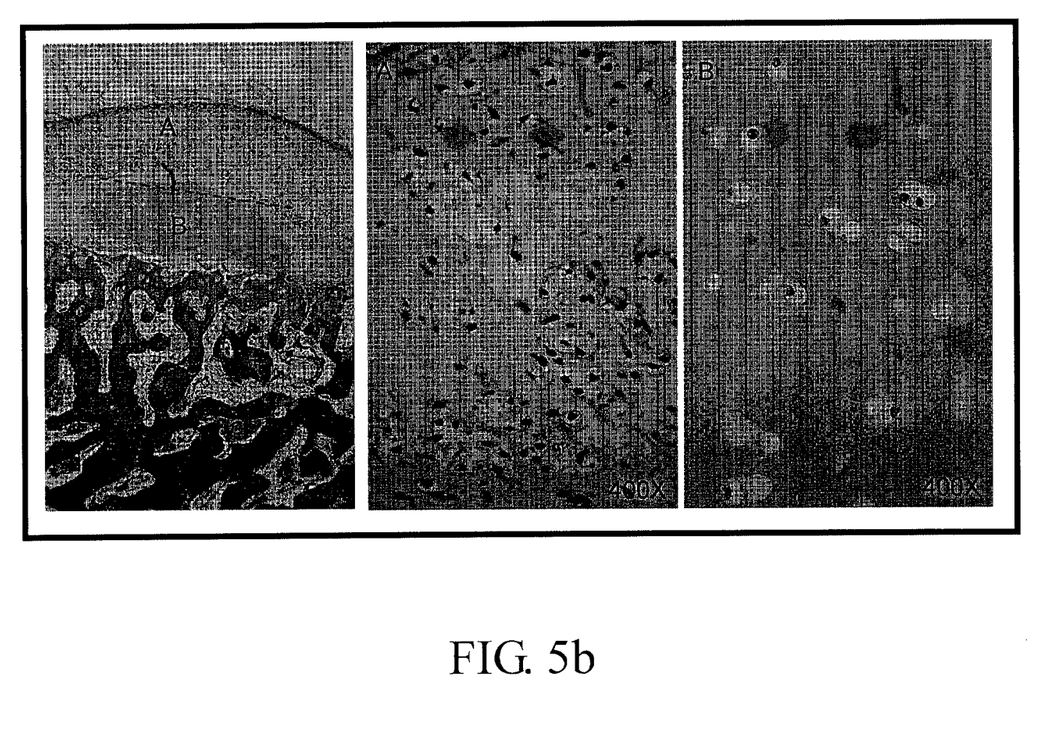
FIG. 5b is a microscopic photograph showing the cell growth of an enzyme-treated cartilage and bone tissues which had been implanted into mouse subcutaneous tissues for one month in one embodiment.

The implanted cartilage and bone tissues were respectively taken out after 1 month and sliced and dyed to obtain microscopic photographs as shown in FIGS. 5a and 5b.

FIG. 5a shows the control group without enzymatic treatment and FIG. 5b shows the experimental group after the enzymatic treatment. The cartilage tissue is shown in the upper region A of the dotted line. According to the results shown in FIGS. 5a and 5b, cell proliferation was not apparently shown in the untreated cartilage tissue, while the enzyme-treated cartilage tissue showed cell proliferation. It is apparent that the enzymatic treatment was able to enhance cell proliferation and it is predictable that the enzymatic treatment is to tissue repair.

Example 2

In Vitro Experiment of Cartilage and Bone Tissues

Three 8 mm-diameter hollow cylinders were individually immobilized on the porcine knee joint containing cartilage and bone tissues (12 mm-diameter shin). The cylinders were then respectively injected with (1) saline, (2) 2.6 U/ml of liberase solution (Roche), and (3) 5.2 U/ml of liberase solution (Roche) with syringes. After 20 minutes, the fluids in the cylinders were extracted out with syringes. Each treated cartilage and bone tissue was washed with saline and sliced and dyed (Hematoxylin & Eosin) to obtain the microscopic photographs as shown in FIGS. 6a, 6b and 6c.

Figure 6A:
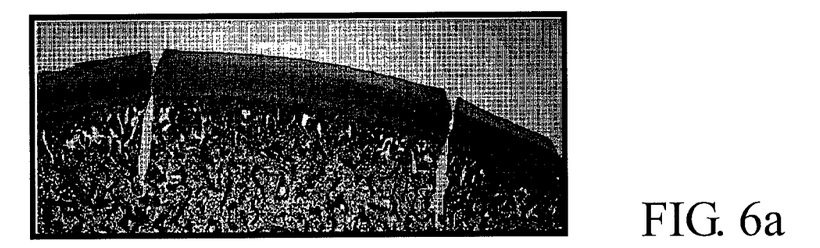
FIG. 6a is a microscopic photograph showing an enzyme-untreated cartilage and bone tissues in one comparative example.
Figure 6B:
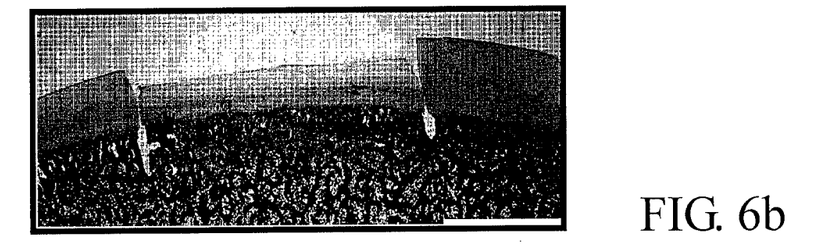
FIG. 6b is a microscopic photograph showing an in vitro 2.6 U/ml-Liberase-treated cartilage and bone tissues in one embodiment.
Figure 6C:
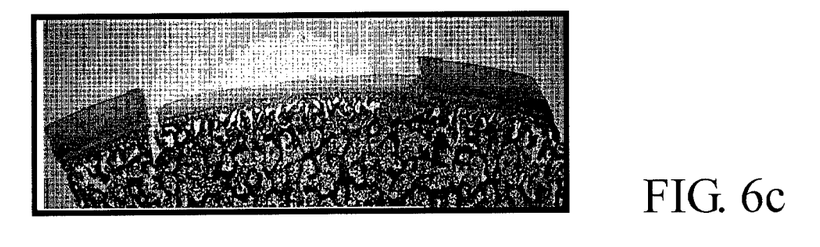
FIG. 6c is a microscopic photograph showing an in vitro 5.2 U/ml-Liberase-treated cartilage and bone tissues in one embodiment.

FIGS. 6a, 6b and 6c show the cartilage and bone tissues treated with saline, 2.6 U/ml of liberase solution and 5.2 U/ml of liberase solution, respectively. According to the results, the cartilage tissue treated with saline did not show clear cell proliferation (FIG. 6a), while the cartilage tissues with the enzyme treatment showed tissue lysis and decreased thickness of the cartilage tissue in a concentration-dependent manner.

Example 3

In Vivo Experiments of Cartilage and Bone Tissues

Two New Zealand white rabbits were cut to expose cartilage tissues of the knee joints of the right hind leg. The exposed cartilage tissues were further cut for immobilization of 2 mm-diameter hollow cylinders respectively. The hollow cylinders were then injected with (1) saline and (2) 2.6 U/ml of liberase solution (Roche) respectively with syringes. After 20 minutes, the fluids in the cylinders were extracted out with syringes. The tissues were washed with saline and the wounds were sutured.

The rabbits were then bred in the laboratory for one month. Then, the cartilage tissues previously treated were taken out and sliced and dyed (Hematoxylin & Eosin) to the microscopic photographs as shown in FIGS. 7a and 7b.

Figure 7A:
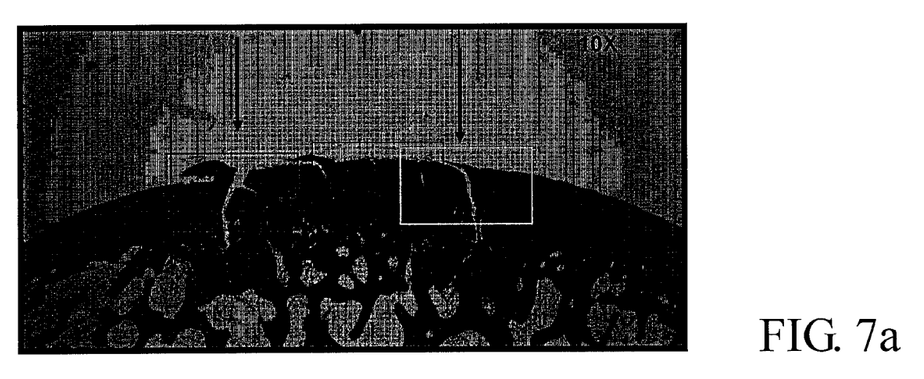
FIG. 7a is a microscopic photograph showing an enzyme-untreated cartilage and bone tissues in one comparative embodiment.
Figure 7B:
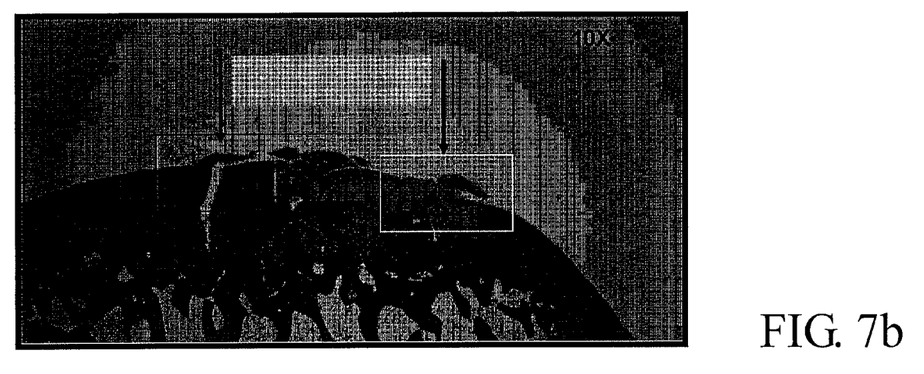
FIG. 7b is a microscopic photograph showing in vivo enzyme-treated cartilage and bone tissues in one embodiment.

FIGS. 7a and 7b show the cartilage and bone tissues treated with saline and 2.6 U/ml of liberase solution, respectively. The arrow points indicate the wounds from the immobilization of the cylinders, and the region between the two arrow points indicates the treated area. As shown in FIG. 7b, the tissue defects (the arrow point) due to the immobilization of the cylinders showed newborn cartilage tissues after the enzyme treatment. The treated area (between two arrow points) also showed newborn cartilage tissues. In contrast, the saline-treated tissue still showed the wounds from the immobilization of the cylinders and the cartilage tissue did not proliferate or regenerate (FIG. 7a)

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A device for enzymatic treatment, comprising:
   a hollow cavity, comprising a first side and a second side opposed to the first side, wherein the first and second sides comprise at least one opening, wherein the device forms a closed space on a tissue surface, and wherein the second side comprises two flanks, and each flank comprises one extrusion thereon.

2. The device as claimed in claim 1, further comprising:
   an infusion element, wherein the infusion element comprises a container part and an infusion opening configured to infuse an enzyme solution through the first side and into the closed space.

3. The device as claimed in claim 1, further comprising:
   an extraction element, wherein the extraction element comprises an extraction part and an extraction opening for extracting fluids through the second and first sides and out from the closed space.

4. The device as claimed in claim 1, wherein each extrusion extends 3-5 mm from the respective flank of the second side.

5. The device as claimed in claim 1, wherein each extrusion is 3-5 mm from the end of the second side.

6. The device as claimed in claim 1, further comprising:
an auxiliary element, wherein the auxiliary element comprises a cap body and an opening for assisting the immobilization of the device on the tissue surface.

7. The device as claimed in claim 1, wherein the second side comprises a biocompatible material.

8. The device as claimed in claim 7, wherein the biocompatible material comprises polyether ether ketone (PEEK), stainless steel or silicone.

9. The device as claimed in claim 1, wherein the tissue comprises cartilage tissues, bone tissues or nerve tissues.

10. The device as claimed in claim 1, further comprising an enzyme solution comprising one or more enzymes selected from the group consisting of a collagenase, a hyaluronidase, a trypsin, a lipase and a proteinase.

11. A kit for treatment of tissue defects, comprising the device as claimed in claim 1 and an enzyme solution.

12. The kit as claimed in claim 11, wherein the enzyme solution comprises one or more enzymes selected from the group consisting of a collagenase, a hyaluronidase, a trypsin, a lipase and a proteinase.

13. The kit as claimed in claim 11, wherein the concentration of the enzyme solution is 2-5 U/ml.

* * * * *